(12) United States Patent
Johnsen

(10) Patent No.: US 10,456,232 B2
(45) Date of Patent: Oct. 29, 2019

(54) TILTABLE IMPLANTABLE MEDICAL DEVICE

(71) Applicant: COOK MEDICAL TECHNOLOGIES LLC, Bloomington, IN (US)

(72) Inventor: Jeppe D. Johnsen, Froerup (DK)

(73) Assignee: Cook Medical Technologies, LLC, Bloomington, IN (US)

( * ) Notice: Subject to any disclaimer, the term of this patent is extended or adjusted under 35 U.S.C. 154(b) by 320 days.

(21) Appl. No.: 15/292,263

(22) Filed: Oct. 13, 2016

(65) Prior Publication Data

US 2017/0100230 A1 Apr. 13, 2017

(30) Foreign Application Priority Data

Oct. 13, 2015 (GB) .................................. 1518085.4

(51) Int. Cl.
*A61F 2/01* (2006.01)
*A61B 17/12* (2006.01)

(52) U.S. Cl.
CPC .......... *A61F 2/01* (2013.01); *A61B 17/12109* (2013.01); *A61B 17/12145* (2013.01); *A61B 17/12163* (2013.01); *A61F 2002/016* (2013.01); *A61F 2210/0014* (2013.01); *A61F 2220/0025* (2013.01); *A61F 2230/0006* (2013.01); *A61F 2230/0071* (2013.01); *A61F 2230/0093* (2013.01); *A61F 2250/0062* (2013.01)

(58) Field of Classification Search
CPC ................. A61F 2/01; A61F 2002/016; A61B 17/12109; A61B 17/12145; A61B 17/12163
See application file for complete search history.

(56) References Cited

U.S. PATENT DOCUMENTS

| 5,669,933 A | 9/1997 | Simon et al. |
| 8,252,018 B2 | 8/2012 | Valaie |
| 8,333,926 B2 | 12/2012 | Tanaka et al. |

(Continued)

FOREIGN PATENT DOCUMENTS

| EP | 1974692 | 10/2008 |
| EP | 2496174 | 9/2012 |

(Continued)

OTHER PUBLICATIONS

European Communication for Application No. EP16275110.1-1651, dated Oct. 20, 2017 (5 Pages).

(Continued)

*Primary Examiner* — Ashley L Fishback
(74) *Attorney, Agent, or Firm* — Brinks Gilson & Lione

(57) ABSTRACT

The implantable medical device includes at least one frame having a rounded shape and formed of a plurality of rounded legs. In one embodiment, the device includes two frames having similar rounded shapes and coupled to one another by means of a flexible coupling. The flexible coupling enables the frames to tilt relative to one another and relative to a vessel in which the device is deployed. The rounded nature of the frames enables the frames to tilt in the vessel while retaining proper contact to the vessel wall and the functional characteristics of the frames. The device may have just one frame in some embodiments and three or more frames in other embodiments. The device may be a filter, an occluding device or any other suitable medical device.

20 Claims, 5 Drawing Sheets

(56) References Cited

U.S. PATENT DOCUMENTS

| | | |
|---|---|---|
| 8,486,105 B2 | 7/2013 | Demond et al. |
| 9,345,564 B2 | 5/2016 | Johnsen |
| 2008/0275488 A1 | 11/2008 | Fleming |
| 2008/0275490 A1 | 11/2008 | Fleming |
| 2011/0137335 A1 | 6/2011 | Hallisey |
| 2011/0251629 A1 | 10/2011 | Galdonik et al. |
| 2013/0238010 A1 | 9/2013 | Johnson et al. |
| 2013/0345739 A1 | 12/2013 | Brady et al. |

FOREIGN PATENT DOCUMENTS

| | | |
|---|---|---|
| EP | 2777602 A1 | 9/2014 |
| WO | WO2004/082532 A1 | 9/2004 |
| WO | WO2005/102439 A2 | 11/2005 |
| WO | WO 2009/032834 A1 | 3/2009 |

OTHER PUBLICATIONS

European Communication for Application No. EP16275110.1-1651, dated Feb. 10, 2017 (7 Pages).

Combined Search and Examination Report for GB1518085.4, dated Mar. 11, 2016.

TILTABLE IMPLANTABLE MEDICAL DEVICE

CROSS-REFERENCE TO RELATED APPLICATIONS

This application claims the benefit of priority under 35 U.S.C. § 119(a) to Great Britain Patent Application No. GB 1518085.4, filed Oct. 13, 2015, which is hereby incorporated by reference in its entirety.

TECHNICAL FIELD

The present invention relates to an implantable medical device assembly for deployment in a vessel of a patient, for instance in the vena cava. The assembly is, in the preferred embodiment, a vascular filter. The teachings herein, though, are applicable to other types of medical device such as but not limited to occlusion devices and to medical devices suitable to vessels other than the vena cava.

BACKGROUND OF THE INVENTION

Implantable medical devices are well known in the art for treating a variety of medical conditions. These may be, for instance, stents, stent grafts, vascular filters, vascular occluders, as well as prosthetic elements such as supplemental or replacement valve elements and so on. It is important for such implantable medical devices to be deployed in a vessel in a manner that they seal properly with the vessel wall and that they retain a good seal over time. While this is possible with many designs of implantable medical device, some devices have shapes and structures which can tilt within the vessel, potentially leading to loss of sealing to the vessel wall and possible migration of the device. The risk of tilting is notable with devices such as vascular filters and occluders, which tend to have non-cylindrical structures, particularly being conical in shape. It is common for such devices to include elements intended to maintain the filter or occluder properly aligned in the vessel, although such measures do not necessarily achieve their intended function. In some cases it is also desirable to have a plurality of device units arranged in series, for instance a series of filtering elements, for optimising the performance characteristics of the device. A structure of such a type is longer than a single unit and it is not unusual for a multi-unit structure device to be deployed in a curved vessel, leading to considerations of proper orientation of each unit within the vessel.

Examples of known vascular filter assemblies are disclosed in US-2008/0275490, US-2013/0345739, US-2013/0238010, US-2011/0251629, U.S. Pat. Nos. 8,486,105 and 8,252,018.

DISCLOSURE OF THE INVENTION

The present invention seeks to provide an improved medical device and in particular a device which is able to tilt in a patient's vessel. The preferred embodiments are in the form of a vascular filter having a plurality of filtering units connected in series. The teachings herein are, though, applicable to a variety of medical devices and not just to filters.

According to an aspect of the present invention, there is provided an implantable medical device including a first capture element formed of a frame of curved leg elements arranged substantially in a sphere with an end opening, the frame providing a material capture chamber therein accessible through the opening; a coupling member attached to the frame wherein the coupling member is at least partially flexible; and a stabilization member attached to the coupling member for stabilizing the capture element, wherein the stabilization member is a second capture element formed of a frame of curved by elements arranged substantially in a sphere with an end opening, the frame providing a material capture chamber therein accessible through the opening, and wherein the first and second capture elements have their openings facing a common direction.

As will become apparent from the specific description which follows, the spherical or rounded shape of the capture element enables it to tilt in a vessel without losing effective contact with the vessel wall and while maintaining capturing efficiency. The skilled person will appreciate that the frame of the capture element need not be precisely spherical and that this will also be affected by the operating conditions of the device in situ in a patient. The capture element is preferably of generally spherical shape, such that it has only a gently varying diameter at a variety of different orientations.

Preferably, the frame of the capture element has the general form of a sphere when laterally compressed to 66 to 80 percent of a maximum unrestrained lateral diameter of the frame. In a preferred embodiment, the frame of the capture element has the form of a sphere when laterally compressed to substantially 75 percent of a maximum unrestrained lateral diameter of the frame.

Advantageously, the capture element has a substantially uniform diameter over a range of angles around a centre point of the capture element. Preferably, the capture element is generally spherical when laterally compressed to around 75% of its maximum expanded diameter. The capture element is preferably tiltable to up to 60 degrees while retaining capture function, in some embodiments the maximum angle of tilt is of 50 or 45 degrees.

In an embodiment, the capture element has a substantially spherical shape over at least a part of an outer surface thereof.

The stabilisation member preferably stabilises the orientation of the capture element. Advantageously, the stabilisation member and the coupling member limit the angle of tilt of the capture element. The stabilisation member and the coupling member may limit an angle of tilt of the capture element to a permitted range of tilt angles, as indicated above.

In a practical embodiment, the coupling member is attached to the capture element through the opening of the capture element. For instance, the coupling member may be attached to an internal surface of the capture element at an attachment point substantially opposite the opening.

Advantageously, the coupling member is rigidly attached to the capture element at the point of attachment.

The coupling member may be attached at an angle substantially perpendicular to a plane of the internal surface at the point of attachment. Advantageously, the coupling member is rigidly attached to the second capture element.

The coupling member may have a limited range of flexibility.

The preferred assembly is preferably formed of two similar or identical material capture elements, in practice arranged in series. For this purpose, the coupling member is preferably attached to an internal surface of the first capture element through the opening of the first capture element and to an external surface of the second capture element opposite the opening of the second capture element. The assembly can therefore provide dual material capture elements able to capture more material and/or to be more stable in a vessel. The material capture elements may be structured to have equivalent capture characteristics, for instance filtering characteristics, or to have different capture characteristics, for instance with one providing relatively coarse filtering and the other relatively fine filtering.

Other embodiments may have more than two material capture elements, for instance three or more arranged in series and connected by coupling members between adjacent capture elements in the series.

In preferred embodiments, the frame of the or each capture element is formed from a plurality of curved frame legs extending from a common point to a perimeter of the opening. The frame legs may curve radially inwardly adjacent the perimeter of the opening.

The frame of the or each capture element may be made of a self-expanding material.

In preferred embodiments, the device is a vascular filter.

Other features and advantages of the teachings herein will become apparent from the following description of the preferred embodiments.

BRIEF DESCRIPTION OF THE DRAWINGS

Embodiments of the present invention are described below, by way of example only, with reference to the accompanying drawings, in which.

DESCRIPTION OF THE PREFERRED EMBODIMENTS

Figure 1:
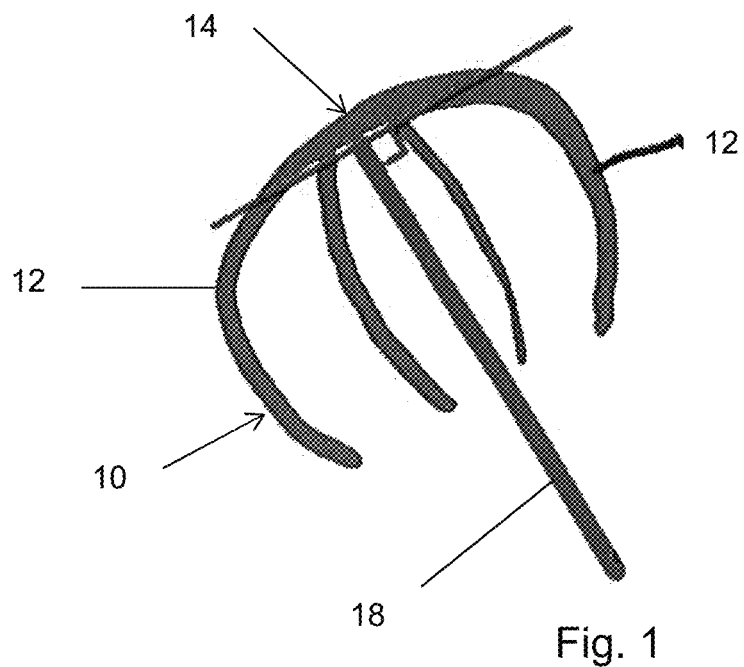
FIG. 1 is a schematic diagram showing a side perspective view of an embodiment of a part of an implantable medical device assembly according to the invention.

It is to be understood that the drawings are schematic only and do not show the elements in proportion. The skilled person will readily appreciate the typical dimensions and proportions of the various elements depicted and will also know that these will generally also vary in dependence upon the nature of the vessel in which the device is to be implanted.

The embodiments described below and shown in the drawings are directed to an implantable medical device which in the preferred embodiments is a vascular filter for implantation, for example, in the vena cava. The stature shown in the drawings can readily be adapted as an occluder, for example by attaching to the legs of the frame structure a cover of occluding material of known type. The skilled person will appreciate also that the teachings herein could be used for other medical implantable device assemblies.

Figure 2:
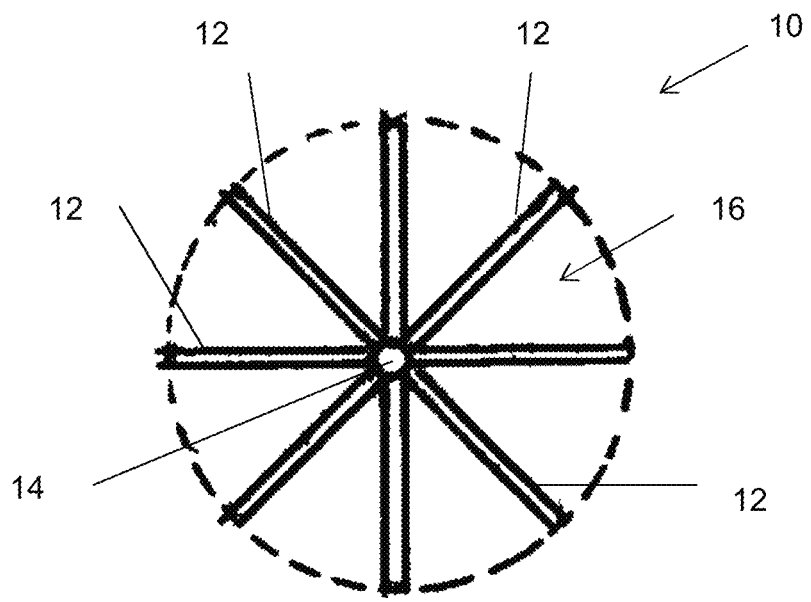
FIG. 2 is a plan view of the device of FIG. 1.

Referring first to FIG. 1, this shows a side elevational view of a part of a preferred embodiment of implantable medical device assembly according to the teachings herein. The device includes a frame 10 which has a rounded or generally round shape. More specifically, the frame 10 is formed of a plurality of legs 12 which extend from a common centre point or hub 14 and curve, in this embodiment, along a generally even radius, further details being described below. The legs 12 are preferably evenly spaced from one another around the hub 14, in the manner depicted in FIG. 2. The legs 12 are preferably substantially the same as one another, that is have the same length, same maximum radius and are made of the same materials, with the same cross-sectional dimensions, so that they behave similarly to one another.

The number of legs 12 can be chosen in dependence upon, in this embodiment, the degree of filtration which it is desired to achieve. The number of legs 12 determines the size of the gaps 16 between adjacent legs 12 and as a consequence the size of particles which will be trapped by the legs 12. In the example shown, the frame has six legs 12, though in other embodiments it could fewer while in other embodiments it could have more than six legs.

The hub 14 could simply be formed as the junction of the various legs 12 to one another but in other embodiments is a disk like element from which the legs 12 extend and to which the connector 18 can be attached. Of course, the hub need not be circular in shape.

Figure 3:
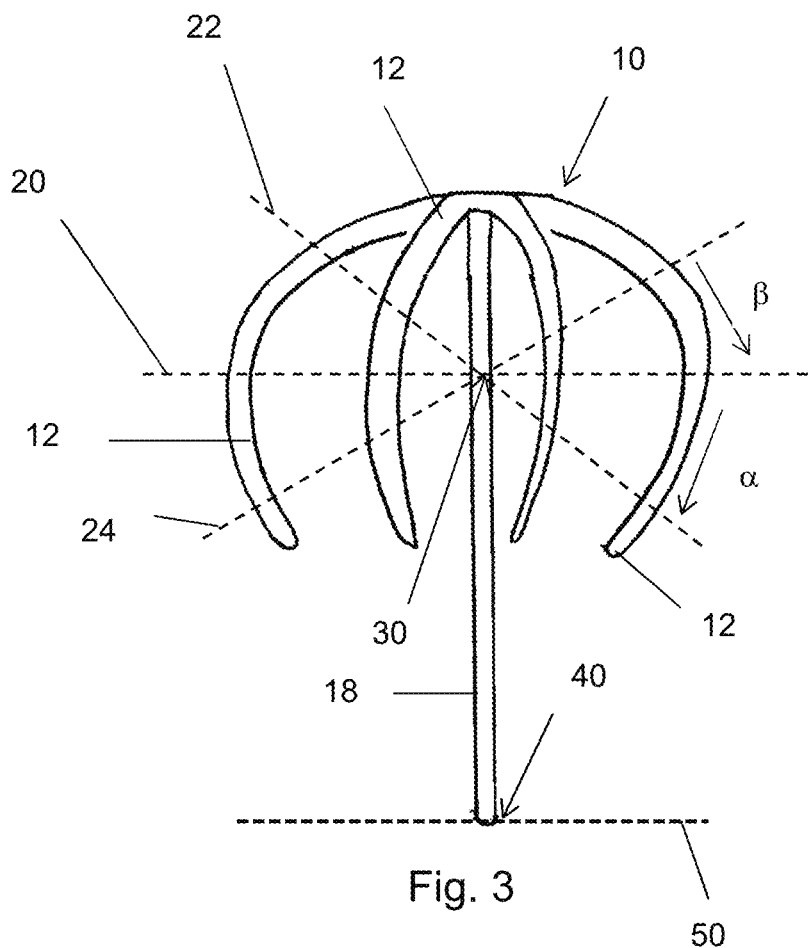
FIG. 3 is a side elevational view of the embodiment of device of FIGS. 1 and 2.

Referring now to FIG. 3, this shows a side elevational view of the frame 10 with superimposed thereon a plurality of indicative diameter lines 20, 22, 24. The line 20 extends across what could be described as a transverse or horizontal line of the frame 10, the flexible connector 18, described in further detail, extending in what could be said to be a longitudinal or vertical direction. The frame 10 is shown in a partially compressed state, particularly compressed to around 75% of its maximum, unrestrained, diameter. In an example, for a device designed to fit into a vessel of diameter between 10 to 30 millimeters, the frame 10 will have a generally spherical shape when compressed laterally (inwardly along the line 20) to around 22.5 centimeters. The skilled person will appreciate that there may be deviations from this example, in that the frame could be generally spherical when compressed, say, to between 66% to 80% of its maximum unrestrained lateral diameter in other embodiments. Line 22 is disposed in this example at an angle $\Omega$, while line 24 extends at an angle $\beta$, both of which are about 45 degrees from the horizontal, that is from line 20. Lines 22 and 24 could be described as lines of tilt and as will be apparent form FIG. 3, and also the other Figures, the frame 10 has a substantially uniform diameter over the range of these angles $\beta$, $\Omega$ and its opening into the body of the frame remains open and in practice able to receive flow of blood from the vessel. Angles $\beta$, $\Omega$ could be chosen to be different, for instance from 30 degrees to 60 degrees or more, thereby changing the possible maximum tilt angle of the frame in a vessel, in dependence upon the nature of the vessel in which the device is intended to be deployed.

The frame 10, specifically the legs 12, could be made of any suitable material although in the preferred embodiments is made of stainless steel, a cobalt chromium nickel alloy such as Elgiloy® or Phynox®, a super alloy such as a shape memory alloy, typically Nitinol. It is preferred that the frames are self-expanding.

Extending from the centre point or hub 14 is the flexible coupling member 18, which preferably extends perpendicularly from the plane of the hub 14 through the centre of the legs 12 in a direction which could be described as a distal direction from the frame 10. The connector 18 is preferably rigidly connected to the hub 14 of the frame 10, such that tilting of the frame 10 is achieved solely by flexure of the connector 18, rather than by tilting or pivoting of the connector 18 relative to the frame 10.

The connecting element 18 could be made of a wire, a braiding or cable tubing, for example. In a preferred embodiment, the connecting element is formed of a coiled wire, having a form similar to that of a coil spring. In other embodiments, the connecting element 18 may be a simple wire, of sufficient strength to impart a straightening force on the connecting element, and in particular to the frame or frames 10 attached thereto, when implanted in a vessel. The connecting element may be made of (or coated with) any resilient biocompatible material. Examples include spring steel, cobalt chromium alloy, nickel titanium alloy such as Nitinol. In the preferred embodiments, the connecting element 18 generates a restoring force, towards the straight, the same or similar to the opening force generated by the frame arms 12, such that these two forces are substantially balanced. This will provide sufficient force in the connecting element 18 to restrain the tilt of the frame or frames 10. It is preferred that the restoring force generated by the connecting element 18 exceeds the opening force of the frame arms 12 when the connecting element is curved to around 60 degrees, preferably less than this, such as 50 degrees or more preferably 45 degrees. This will in practice limit the amount by which the frames 10 can tilt in a vessel. The skilled person will know how to design the flexibility of the connecting element, by choice of materials, thickness and density of the wire and so on.

In some embodiments the connector 18 may be pivotally connected to the hub 14, for instance by means of a ball joint or the like, having a limited degree of pivotal movement. Provision of a ball joint with limited rotation allows tilting of the frame 10 relative to the connector 18 up to the limit and as a result may use a rigid or less flexible connector element 18.

The components seen in FIGS. 1 and 3 form a part of the implantable medical device, which in practice will be provided also with a stabilisation member attached to the distal end 40 of the coupling member 18. In its simplest form, a stabilisation member could comprise a disc, ring, arms or other structure 50 extending transversely from the distal end 14 of the coupling member 18. The stabilisation member may have a radius equivalent to the maximum radius of the material capture frame 10 although it could be less than this, allowing or contributing to tilt of the frame 10. The stabilisation member 50, together with the flexible coupling member 18, can therefore limit the angle of the tilt of the capture element frame 10. This is, as the skilled person will appreciate, preferably within the permitted range of tilt angles, as described in further detail below.

As will be apparent from FIG. 3, the stabilisation member 50 is located opposite the hub 14 and such that the legs 12 of the frame 10 extend towards the stabilisation member 50.

Figure 4:
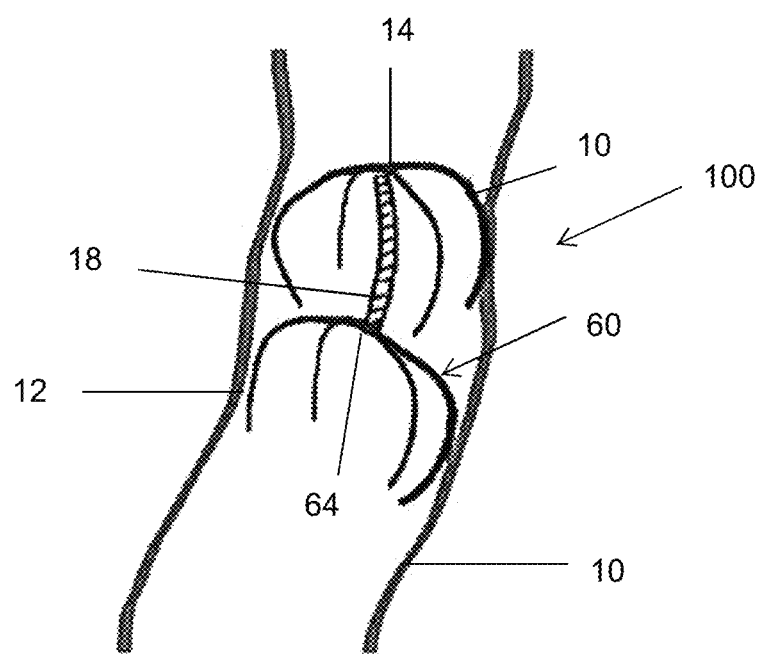
FIGS. 4 to 7 are side elevational views of an embodiment of medical device assembly having two material capture elements, disposed in a vessel.
Figure 5:
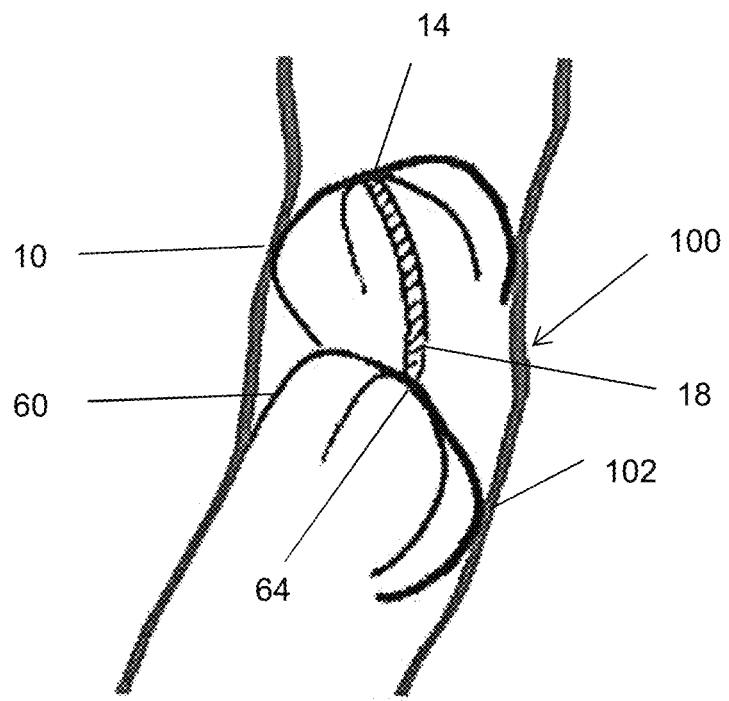
Figure 6:
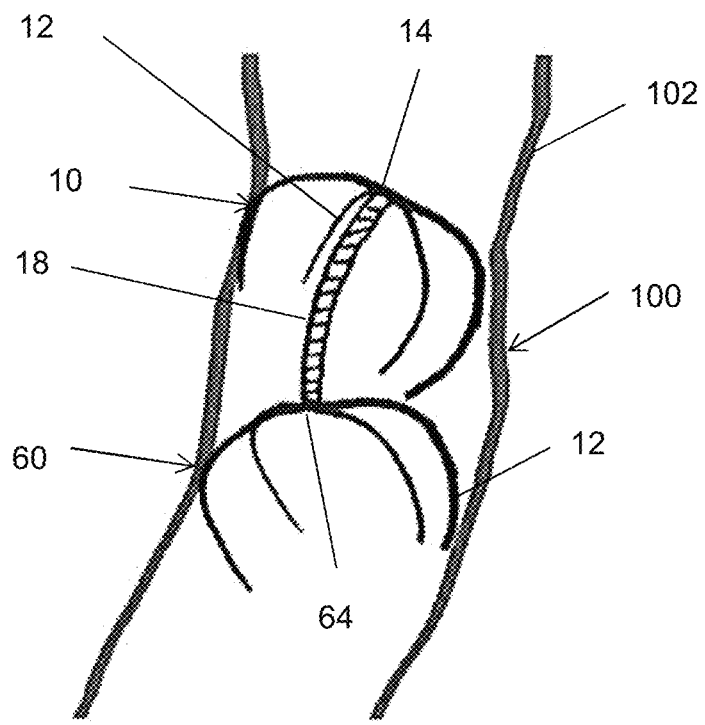

In the preferred embodiment, and as shown in FIGS. 4 to 6, the stabilisation member is a second capture element 60 having a frame and legs 12 of substantially similar construction to the frame 10 of the first capture element. The legs 12 of second capture element 60 extend in the same direction as the frames 12 of the first frame 10, such that both frames 10, 60 face in the same direction, typically with their open ends facing the direction of flow of fluid in the vessel. The coupling member 18 is coupled to the outside surface (as determined by the direction of the legs 12) of the hub 14 of the frame 60, as will be immediately apparent from FIGS. 4 to 7.

It is not excluded that the frame 60 may differ from the frame 10, for example in relation to its filtering characteristics, in which case it may have a differing number of legs 12. The frame 60 may also or in the alternative differ in terms of its relative size, in which case it may expand to a different diameter than the diameter of the frame 10. It is, however, preferred that the second frame 60 has the same rounded shape as the frame 10 and as described above.

The connector 18 is, likewise, rigidly connected to the hub 64 of the frame 60, such that any tilting between the two frames 10 and 60 is achieved through the flexibility of the coupling member 18, although in some embodiments there may be provided a flexible coupling between the coupling member 18 and one of or both of the frames 10, 60, of a type mentioned above.

FIGS. 4 to 7 show the implantable medical device 100 with the dual frames 10, 60, positioned within a vessel 102. As can be seen from a comparison of FIGS. 4 to 6 in particular, the frames 10, 60 can adopt a variety of tilt positions within the vessel, including tilt angles to extend non-parallel to a longitudinal axis of the vessel, and relative to one another, as a result of their rounded shape and the flexible connection between the two frames 10, 60. As will be apparent from these Figures, the frames 10, 60, given their rounded shapes, will maintain good contact with the vessel wall even when tilted in the vessel and relative to one another. As the skilled person will appreciate, as the legs 12 have free ends which are spaced from one another, in the embodiments providing an opening into the chambers of the filters which are at least 50% of the overall diameter of the frames 10, 60, so blood can flow into the chambers formed by the legs 12 even when the frames 10, 60 are tilted. As a result, the frames 10, 60 retain optimal clinical performance, in this embodiment filtering of blood in the vessel 102, even when in the configurations shown in FIGS. 4 to 8.

As will be apparent from FIGS. 4 to 6, the flexible connector 18 allows for constrained rotational movement of each filter frame 10, 60, in practice also allowing each filter frame 10, 60 to adapt to the anatomy of the vessel, in this example the vena cava. The connecting element 18 maintains the same or substantially the same distance between the frames 10, 60 and in particular between the hubs 14, 64 of the two frames. The length of the connecting member 18 preferably matches the diameter of the filter frames 10, 60 such that these do not collide at any of the angles of tilt allowed for the frames 10, 60, as described in further detail below. The rigid coupling of the connecting member 18 to the frames 18, in the preferred embodiment, has a centring effect on the frame bodies 10, 60, as the flexible portion 18 is in a relaxed state when the frames 10, 60 are straight inside the vessel 102, that is with the connecting member 18 following the centreline of the vessel 102 and with the hubs 14, 64 oriented substantially perpendicularly to that centreline. As a result, the frames 10, 60 are biased towards to a non-tilted configuration, which will assist in limiting the actual tilt of the frames 10, 60 in situ.

Figure 7:
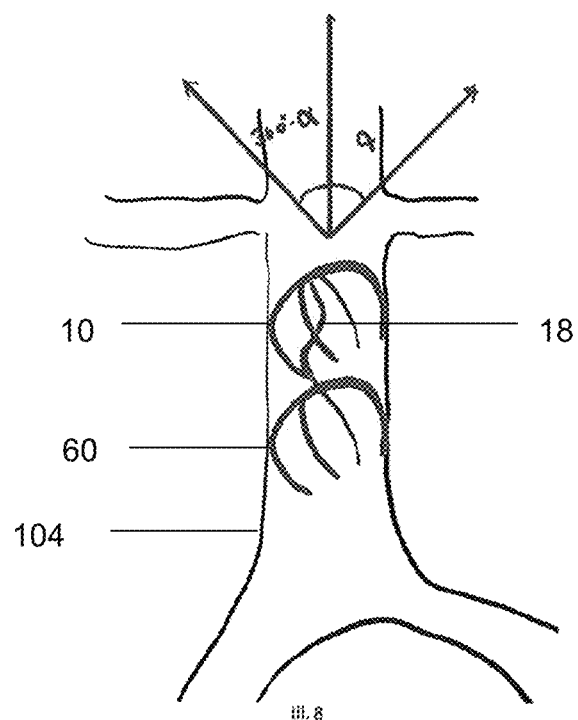

Referring to FIG. 7 this depicts the medical device 10, 60 positioned within the vena cava 104 with the maximum desired angle of tilt indicated by a in the Figure. The maximum angle of tilt a may be 60 degrees but advantageously 50 degrees or even 45 degrees.

Figure 8:
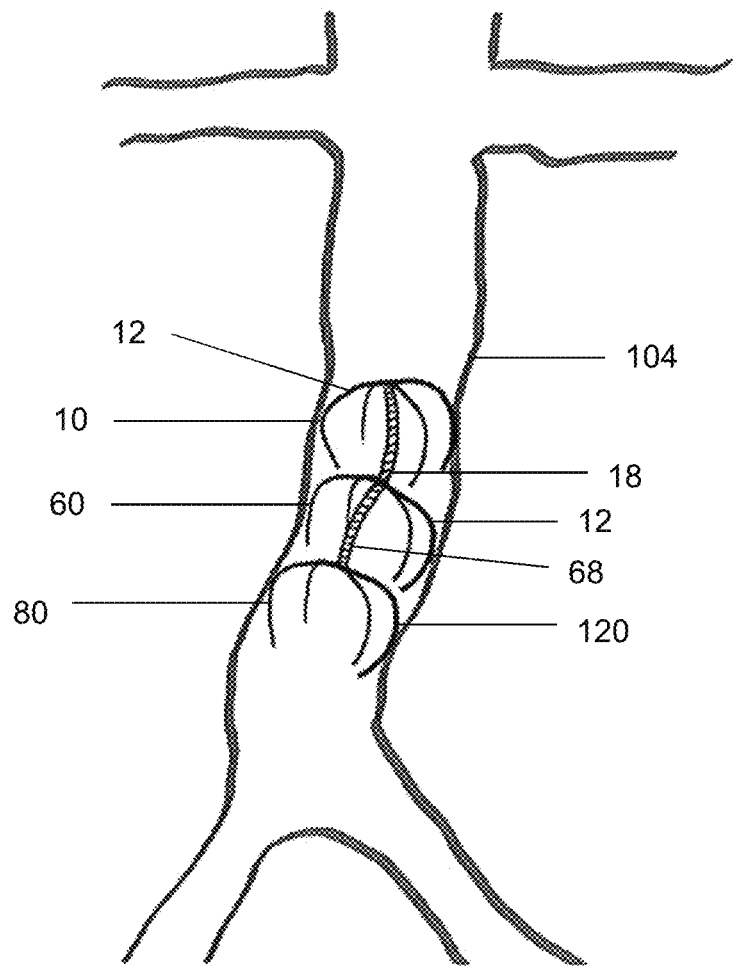
FIG. 8 is a side elevational view of an embodiment of medical device assembly having three material capture elements, disposed in a vessel.

Referring now to FIG. 8, this shows another embodiment of assembly in situ in the vena cava 104. In this embodiment, the assembly being formed of three frame elements 10, 60, 80 all preferably having the same rounded or generally spherical characteristics as described above and connected to one another in series by flexible connectors 18, 68, which again are preferably similar and have similar functional characteristics. As explained above, though, the frames 10, 60, 80 may have different characteristics, such as different filtering functionalities (for which they may have differing numbers of legs 12) and potentially different maximum diameters. Similarly, the connectors 18, 68 could have different flexibilities.

As will be apparent from FIG. 8, the frames 10, 60, 80 are able to tilt in the same manner as described above in connection with the embodiments of FIGS. 1 to 7, up to a maximum angle of tilt, while retaining their clinical performance.

It is to be understood that the frames 10, 60, 80 will remain slightly compressed in the vessel in order to impart a force against the vessel wall to ensure positional reliability in use. In practice, the device may be provided with anchoring features to secure the device from caudal migration. Barbs and similar anchoring elements could usefully be provided on some or all of the legs 12.

In summary, the embodiments of implantable medical device disclosed above include at least one frame 10, 60 having a rounded shape and formed of a plurality of curving rounded legs 12. In one embodiment, the device includes two frames 10, 60 having similar rounded shapes and coupled to one another by means of flexible coupling 18. The flexible coupling 18 enables the frames 10, 60 to tilt relative to one another and relative to a vessel 102 in which the device is deployed. The rounded nature of the frames 10, 60 enables them to tilt in the vessel 102 while retaining proper contact to the vessel wall 102 and the functional characteristics of the frames 10, 60. The device may have just one frame 10 in some embodiments and three or more frames 10, 60, 80 in other embodiments. The device may be a filter, an occluding device or any other suitable medical device.

All optional and preferred features and modifications of the described embodiments and dependent claims are usable in all aspects of the invention taught herein. Furthermore, the individual features of the dependent claims, as well as all optional and preferred features and modifications of the described embodiments are combinable and interchangeable with one another.

The invention claimed is:

1. An implantable medical device for deployment in a vessel of a patient, the implantable medical device including a first capture element formed of a first frame of curved leg elements with a first end opening, the first frame providing a material capture chamber therein accessible through the first end opening; a coupling member attached to the frame; and a stabilization member attached to the coupling member for stabilizing the capture element, wherein the stabilization member is a second capture element formed of a second frame of curved leg elements with a second end opening, each of the first frame and the second frame providing a material capture chamber therein accessible through each of the end openings, and wherein the first and second capture elements have their end openings facing a common direction, wherein at least one of the first capture element and the second capture element is configured to tilt at a tilt angle to extend non-parallel to a longitudinal axis of the vessel while maintaining proper contact to a wall of the vessel.

2. The implantable medical device according to claim 1, wherein each of the first frame and the second frame has a rounded shape when laterally compressed to 66 to 80 percent of a maximum unrestrained lateral diameter of each of the frames.

3. The implantable medical device according to claim 1, wherein each of the first frame and the second frame has a rounded shape when laterally compressed to 75 percent of a maximum unrestrained lateral diameter of each of the frames.

4. The implantable medical device according to claim 1, wherein each of the first frame and the second frame has a uniform diameter over an angle of at least 45 degrees from a transverse plane of each of the frames.

5. The implantable medical device according to claim 1, wherein the stabilization member stabilises an orientation of the first capture element.

6. The implantable medical device according to claim 1, wherein the stabilization member and the coupling member limit an angle of tilt of the first capture element.

7. The implantable medical device according to claim 1, wherein the coupling member is attached to the first capture element through the first end opening of the first capture element.

8. The implantable medical device according to claim 1, wherein the coupling member is attached to an internal surface of the first capture element at an attachment point opposite the first end opening of the first capture element.

9. The implantable medical device according to claim 8, wherein the coupling member is rigidly connected to the first capture element at the point of attachment.

10. The implantable medical device according to claim 8, wherein the coupling member is attached at an angle perpendicular to a plane of the internal surface at the point of attachment.

11. The implantable medical device according to claim 1, wherein the coupling member has a flexibility no greater than a flexibility of the first frame.

12. The implantable medical device according to claim 1, wherein the coupling member generates a restoring force on deflection at least as great a restoring force generated on deflection of the first frame.

13. The implantable medical device according to claim 1, wherein the coupling member is attached to an internal surface of the first capture element through the first end opening of the first capture element and to an external surface of the second capture element opposite the second end opening of the second capture element.

14. The implantable medical device according to claim 13, wherein the coupling member is rigidly attached to the second capture element.

15. The implantable medical device according to claim 1, wherein the each of the first frame and the second frame is formed from a plurality of curved frame legs extending from a common point to a perimeter of each of the end openings.

16. The implantable medical device according to claim 15, wherein the frame legs curve radially inwardly adjacent the perimeter of each of the end openings.

17. The implantable medical device according to claim 1, wherein the first frame is made of a self-expanding material.

18. The implantable medical device according to claim 1, further comprising a third capture element, the first, second and third capture elements being coupled in series along the coupling member.

19. The implantable medical device according to claim 1, wherein the device is a vascular filter or plug.

20. An implantable medical device for deployment in a vessel of a patient, the implantable medical device including a first capture element formed of a first frame of curved leg elements with a first end opening, the first frame providing a material capture chamber therein accessible through the first end opening; a coupling member attached to the frame; and a stabilization member attached to the coupling member for stabilizing the capture element, wherein the stabilization member is a second capture element formed of a second frame of curved leg elements with a second end opening, each of the first frame and the second frame providing a material capture chamber therein accessible through each of the end openings, and wherein the first and second capture elements have their end openings facing a common direction, wherein the coupling member is at least partially flexible such that at least one of the first capture element and the second capture element is configured to tilt non-parallelly relative to a longitudinal axis of the vessel, and wherein the at least one of the first capture element and the second capture element is configured to tilt relative to the longitudinal axis by an angle of greater than 0 degree and no more than 60 degrees.

* * * * *